US 6,694,190 B1

(12) United States Patent
Spelman et al.

(10) Patent No.: US 6,694,190 B1
(45) Date of Patent: Feb. 17, 2004

(54) APPARATUS AND METHOD FOR TREATING STRIAL HEARING LOSS

(75) Inventors: Francis A. Spelman, Seattle, WA (US); Timothy J. Johnson, Kent, WA (US); Scott S. Corbett, III, Portland, OR (US); Ben M. Clopton, Bainbridge Island, WA (US)

(73) Assignee: Advanced Lochlear Systems, Inc., Snowqualmie, WA (US)

( * ) Notice: Subject to any disclaimer, the term of this patent is extended or adjusted under 35 U.S.C. 154(b) by 0 days.

(21) Appl. No.: 10/287,989

(22) Filed: Nov. 5, 2002

(51) Int. Cl.[7] .................................................. A61N 1/18

(52) U.S. Cl. ....................................................... 607/57

(58) Field of Search ...................... 600/379; 607/55–57, 607/72–75, 136, 137

(56) References Cited

U.S. PATENT DOCUMENTS 3,751,605 A  *  8/1973  Michelson .................... 607/57
6,045,528 A     4/2000  Arenberg et al. ............. 604/28

OTHER PUBLICATIONS

Schmeidt, "Cochlear potentials . . . Jump Start?", 1993.*
Schmiedt, Richard. A., "Cochlear Potentials in Quiet–Aged Gerbils: Does the Aging Cochlea Need a Jump Start?", chapter 6, pp 91–103. Sensory Research: Multimodel Perspectives, Hillsdale, Erlbaum Assoc. 1993.

* cited by examiner

Primary Examiner—George R. Evanisko
(74) Attorney, Agent, or Firm—Law Office of Timothy E. Siegel; Timothy E. Siegel

(57) ABSTRACT

A bodily implanted charge injection assembly for effecting a voltage difference between a specific body location and surrounding tissue. This assembly comprises a charge injection device that includes a first electrode assembly and a housing defining an interior space substantially enclosing the first electrode assembly and further defining a first opening placed near the specific location. The housing is filled with electrolytic solution. Also, a second electrode assembly is placed in contact with both the electrolytic fluid and the surrounding tissue. In addition, a physical gate assembly is adapted to selectively and controllably occlude the interior space so that either the first opening or the second electrode assembly may be occluded from the first electrode assembly. The physical gate assembly is controlled to drive current through the opening and alternately to refresh the first electrode assembly with current from the second electrode assembly.

1 Claim, 12 Drawing Sheets

MEMS switch closed

MEMS switch open

APPARATUS AND METHOD FOR TREATING STRIAL HEARING LOSS

STATEMENT OF GOVERNMENT SUPPORT

The invention was made with government support under grant number R43DC005531-01 ZRG01. The government has certain rights in the invention.

BACKGROUND OF THE INVENTION

As many as seven million Americans suffer from a form of hearing loss known as strial presbycusis, which is marked by a loss of hearing in all registers and, as the name indicates, is associated with the aging process. In a healthy ear there is a voltage difference across the basilar membrane, the organ that hosts the hair cells. This voltage difference, referred to as "endocochlear potential," causes current to flow through the hair cells. Sound waves cause the hair cells to bend, thereby changing their electrical conductivity and the amount of current that flows through them. This process results in the electrical nerve impulses that are sent to the brain by the auditory nerve.

It appears that the most frequent immediate cause of strial presbycusis is the deterioration of the stria vascularis, a structure that extends along the basilar membrane and produces the ions that create the endocochlear potential. The loss of endocochlear potential appears to result in both an immediate decline in hearing acuity and a gradual deterioration of the structure of the scala media. One potential method of restoring the endocochlear potential is to inject additional charge by means of an electrode. This is difficult, however, because it requires the production of a DC current within the body. The body's interstitial tissues tend to foul and eventually destroy any implanted electrode producing a DC current. Further, metal electrodes either dissolve or become plated with new material when they are driven with DC currents. Because of this, existing therapeutic devices which produce electrical currents within the body, including pacemakers and neural stimulation systems, are driven by charge balanced, biphasic electrical pulses.

SUMMARY

In a first separate aspect, the present invention is a method to increase the endocochlear potential within the ear to restore normal hearing, comprising the implantation of an electrical device in the ear which maintains a voltage offset between the scala media and the surrounding tissue. The device is capable of injecting a unidirectional pulsatile current flow of at least an average of 5 $\mu$A DC current into the scala media for at least thirty days.

In a second separate aspect, the present invention is a bodily implanted charge injection assembly for effecting a voltage difference between a specific body location and surrounding tissue. This assembly comprises a charge injection device that includes a first electrode assembly and a housing defining an interior space substantially enclosing the first electrode assembly and further defining a first opening placed near the specific location. The housing is filled with electrolytic solution. Also, a second electrode assembly is placed in contact with both the electrolytic fluid and the surrounding tissue. In addition, a physical gate assembly is adapted to selectively and controllably occlude the interior space so that either the first opening or the second electrode assembly may be occluded from the first electrode assembly. The physical gate assembly is controlled to drive current through the opening and alternately to refresh the first electrode assembly with current from the second electrode assembly.

In a third separate aspect the present invention is an electrolytic current injection device comprising an electrode and an electrolytic current port. In addition a control and rectification assembly is adapted to apply a biphasic pulse to said electrode, yet produce a pulsatile, unidirectional DC electrolytic current at said electrolytic current port.

The foregoing and other objectives, features and advantages of the invention will be more readily understood upon consideration of the following detailed description of the invention, taken in conjunction with the accompanying drawings.

DETAILED DESCRIPTION OF THE PREFERRED EMBODIMENT

Figure 1:
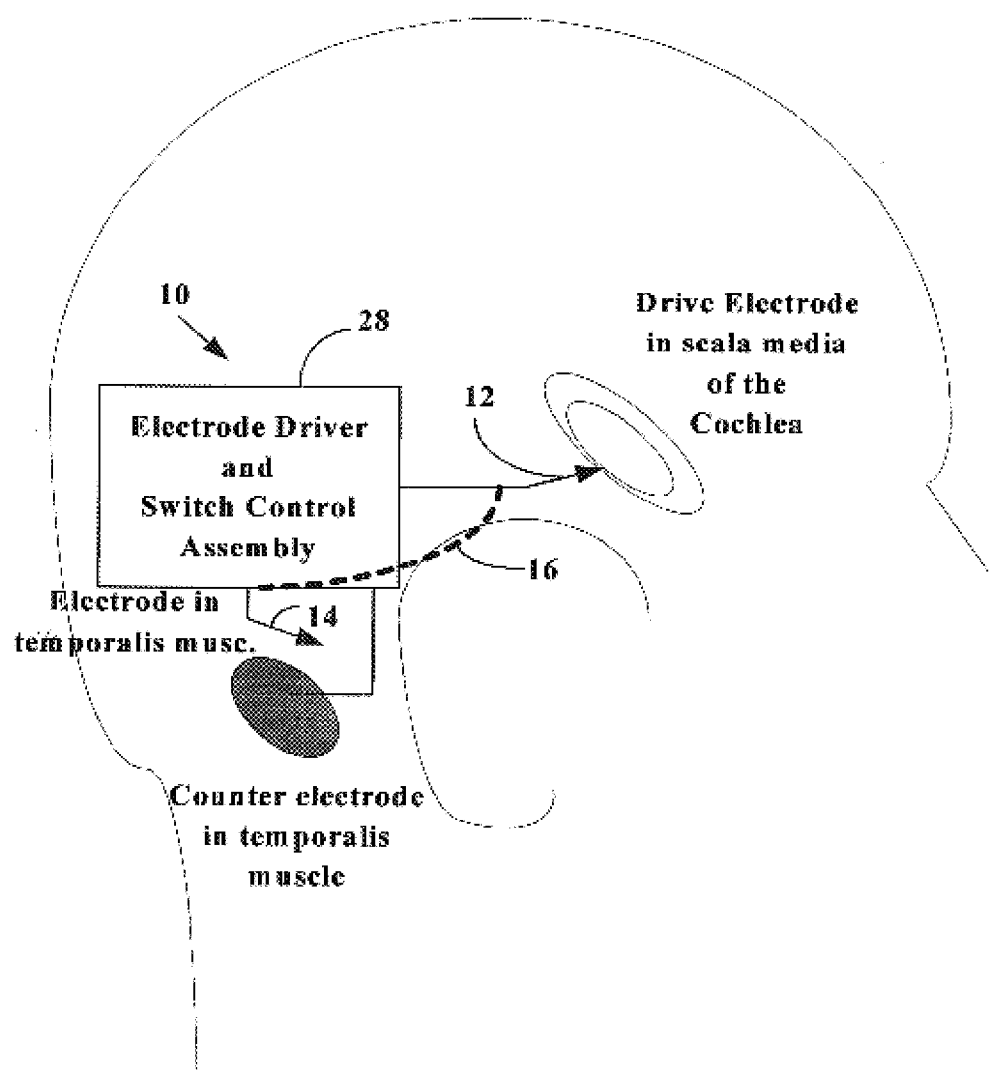
FIG. 1 is an illustration of an implantable charge injection assembly and driver, according to the present invention, shown implanted in the skull.
Figure 2:
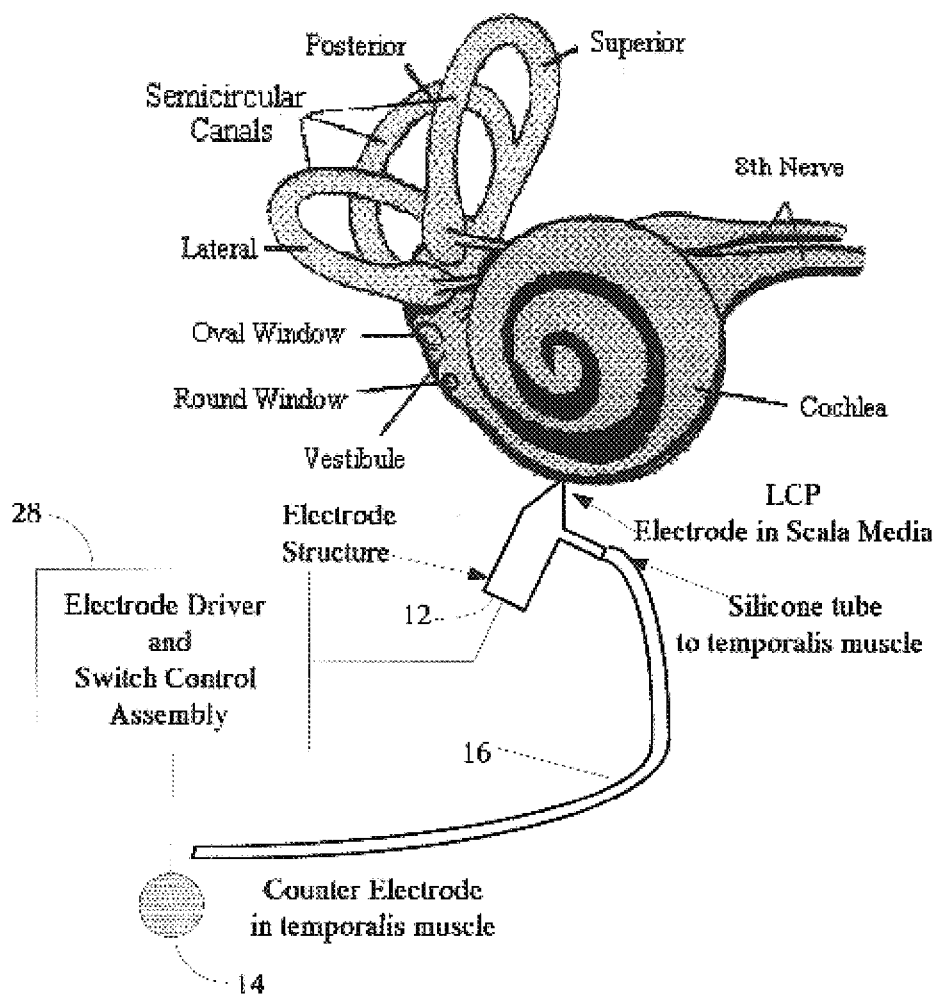
FIG. 2 is an illustration of the implantable charge injection assembly and driver of FIG. 1, shown in relation to the structure of the inner ear.
Figure 3:
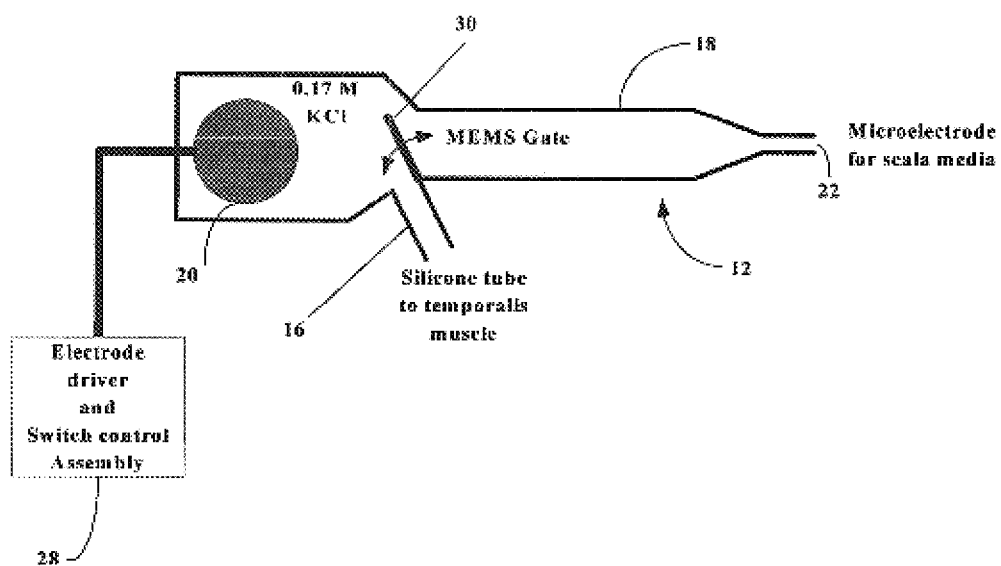
FIG. 3 is an illustration of the implantable charge injection assembly of FIG. 1, shown in greater detail.

Referring to FIGS. 1 and 2, an implantable charge injection assembly 10 according to the present invention, is designed to be implanted in the human skull. A charge injection unit 12 will be placed so that it contacts the scala media of the subject. In one preferred embodiment, the structure of charge injection unit 12 includes an electrolytic fluid-filled liquid crystal polymer (LCP) housing 18 (FIG. 3). The electrolytic fluid is an aqueous solution of _0.17_M KCl to match the potassium concentration of human scala media tissue. Referring to FIG. 3, a primary electrode 20 located in the housing 18 is made of conductive metal plated with IrOx and has a surface area sufficient to sustain a positive current pulse >5 microamperes for >1 second, e.g., of $1.6 \times 10^9 \mu m^2$. Injection unit 12 includes a tip 22 that contacts the scala media and has an interior area that is less than one hundred thousandth that of electrode 20, being between 100 $\mu m^2$ and 10,000 $\mu m^2$. The length of the tip 22 is 0.2 mm to 0.5 mm.

The dimensions of charge injection unit 12 determine the bulk of the DC resistance of unit 12, which equals about 0.1 to 1 megohms, based on a resistivity of 36.7 ohm-cm for 0.17 M KCl at 37° C.

Charge injection assembly 10 includes a tube 16 that extends from unit 12 to a refresh electrode 14 that is embedded in the temporalis muscle, or that may be located in a closed side chamber of the electrode assembly. Tube 16 has an inside diameter of 25 $\mu m$ or more and is filled with KCl liquid of appropriate molarity.

An electrode driver and switch control assembly 28 controls a micro machined gate 30 assembly with flap 32(FIGS. 3 4 and 5), which exposes electrode 20 to either tip 22 or refresh electrode 14. When the gate assembly 30 is positioned to connect electrode 20 to tip 22, assembly 28 drives electrode 20 to cause it to inject charge into the scala media by way of tip 12. When the gate assembly 30 is positioned to connect electrode 20 to the refresh electrode 14, electrodes 20 and 14 will be driven so that electrolytic current flows into and thereby refreshes primary electrode 20, analogous to half-wave rectification. The single bi-state gate could also be replaced by two separate single-state gates operating in opposite phase from one another.

Figure 4:
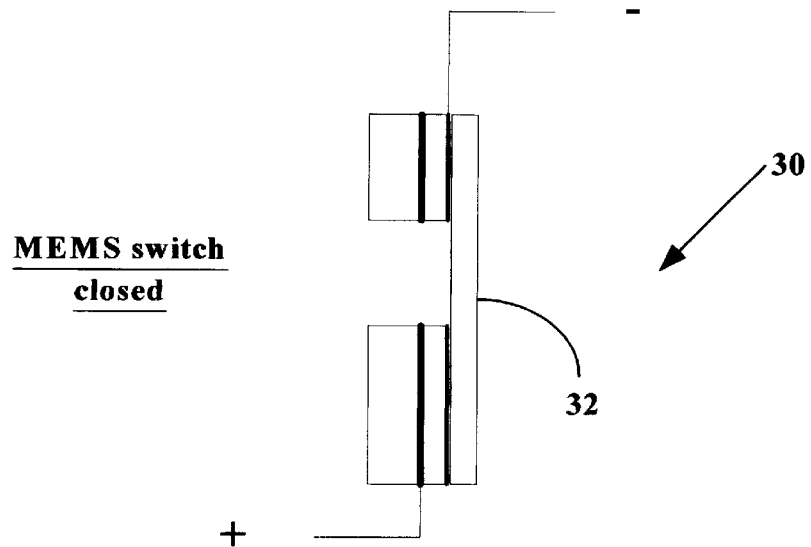
FIG. 4 is a greatly expanded illustration of an electrostatically actuated micro machined gate, in its closed state, as utilized in the present invention.
Figure 5:
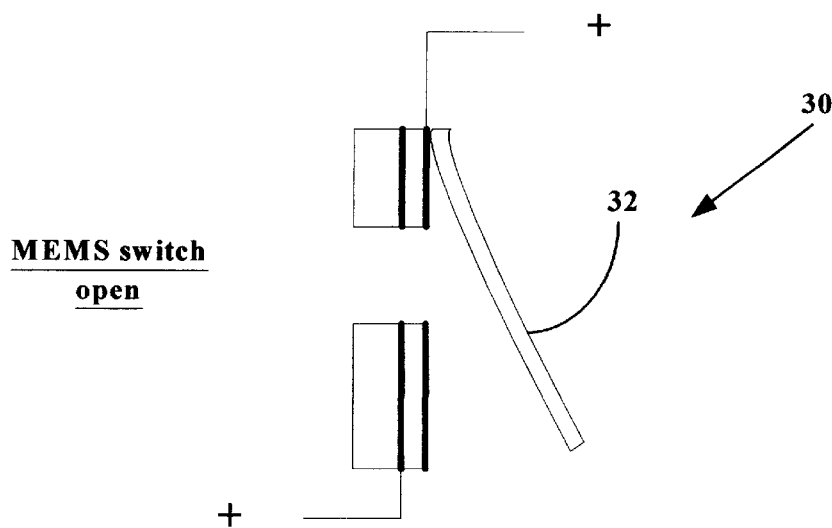
FIG. 5 is a greatly expanded illustration of an electrostatically actuated micro machined gate in its open state, as utilized in the present invention.

Referring to FIGS. 4 and 5, in one preferred embodiment gate 30 is electrostatically actuated. Gate 30 is made by the photolithographic conductive structures on thin sheets of liquid crystal polymer (LCP) combined with the laser micromachining of a small flap 32. The flap 32 is kept closed by maintaining a small opposite charge on electrodes placed on the surfaces of flap 32. The facing electrodes are electrically separated by a surface dielectric. To open the switch, like polarity is applied to both electrodes. By utilizing LCP material, which is thermoplastic, material can be selectively adhered by spot "welding" using an IR laser, or selectively removed using a UV laser, allowing a variety of designs to be implemented. In an alternative approach, the gate is mechanically pre-biased to remain closed. The bias is then overcome electrostatically to actuate the gate.

Figure 6:
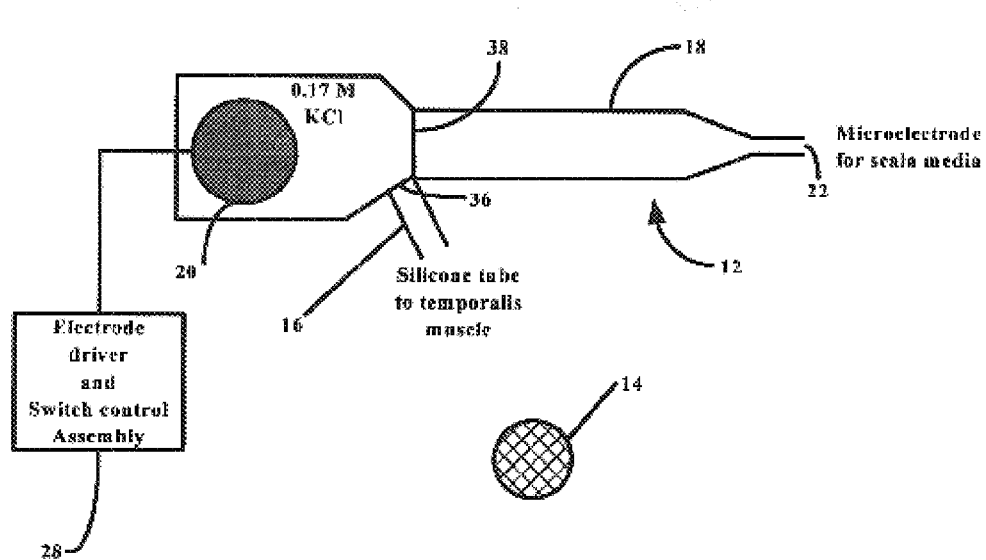
FIG. 6 is an illustration of an alternative embodiment of an implantable charge injection assembly, which includes membranes that controllably and selectively permit the passage of electrolytes.
Figure 7:
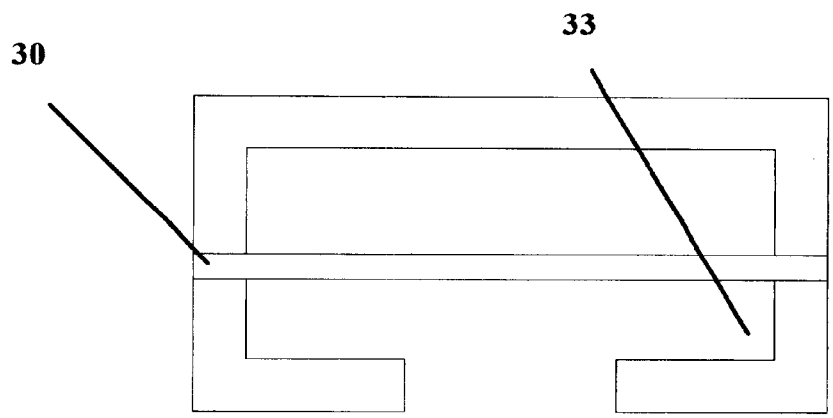
FIG. 7 is an illustration of an additional alternative embodiment of an implantable charge injection assembly, which uses pressure actuated MEMS switches.
Figure 7:
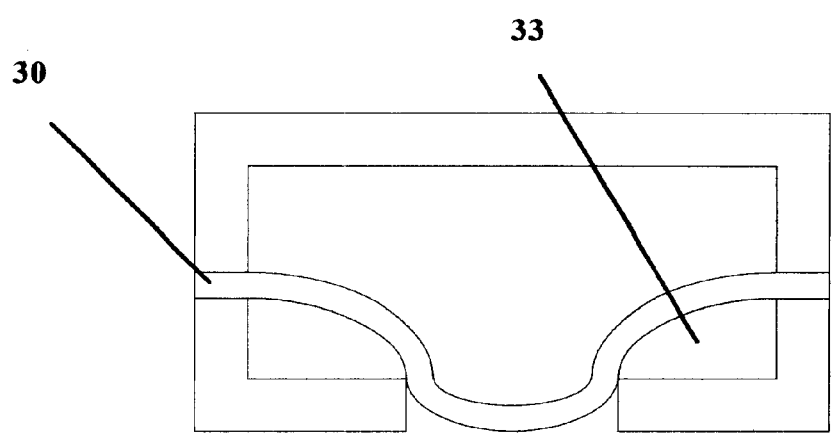

Referring to FIG. 6, in an alternative preferred embodiment, a pair of ion-selective membranes 36 and 38 that permit the flow of positive ions from electrode surface 20 in a direction toward the tip of the electrode 22, while simultaneously allowing the flow of negative ions from electrode 14 and surrounding tissue. In another preferred embodiment the gate is actuated with pressure. Referring to FIG. 7, gate 30 is made with a flexible, insulating membrane that is moved with pressure to open and close the orifice in chamber 33. To close the gate, the pressure above the membrane exceeds that in the chamber. To open the gate the pressure above the membrane is equal to or less than that in the chamber. If the pressure is equal, the elasticity of the membrane produces a restoring force that opens the gate, while if the pressure is less, the pressure differential opens the gate.

Figure 8:
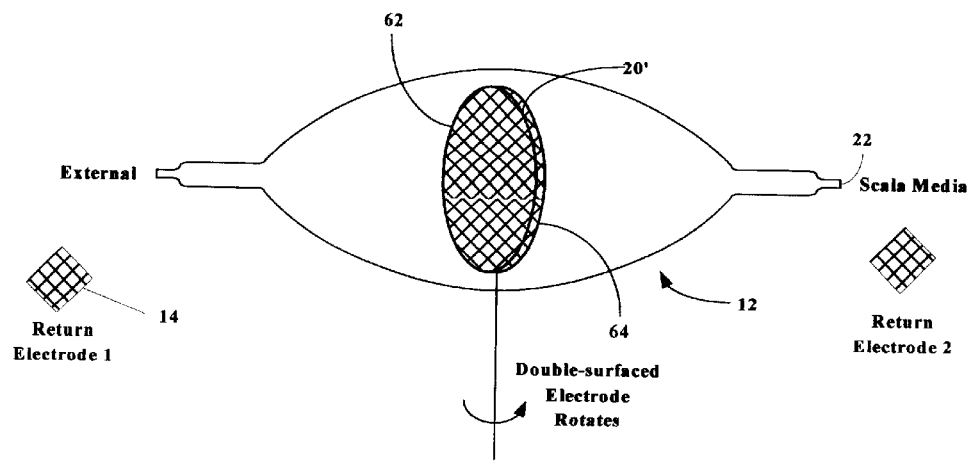
FIG. 8 is an illustration of an additional alternative embodiment of an implantable charge injection assembly, which has a rotatable electrode.

In yet another preferred embodiment, shown in FIG. 8, a primary electrode 20' is rotatable, so that a first face 62 can be refreshed while a second face 64 is actively injecting current into the scala media.

Figure 9:
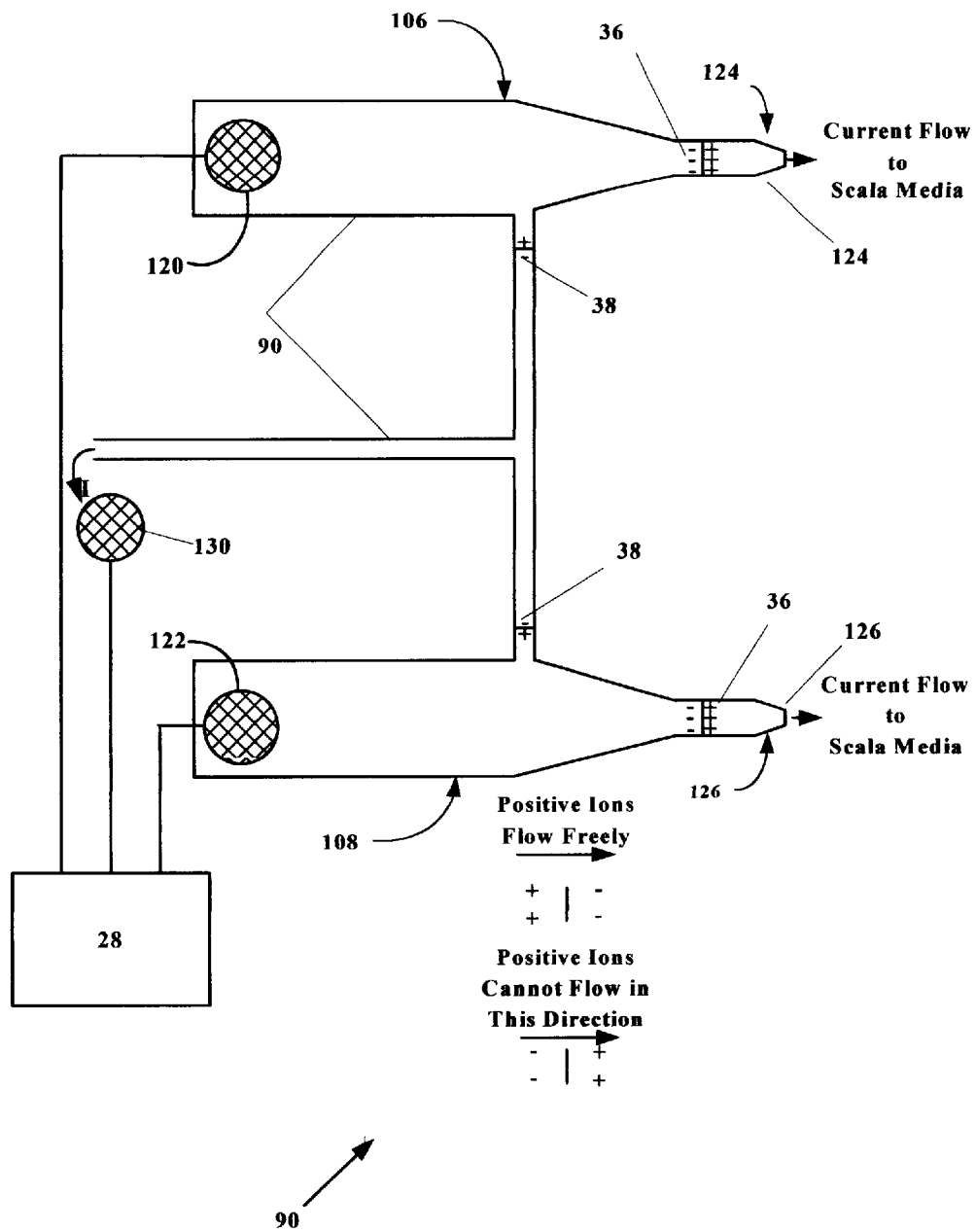
FIG. 9 is an illustration of an additional alternative embodiment of an implantable charge injection assembly, which has two charge injection units.

Electrode 20 (or 20') is capable of passing a current of 10 $\mu A$ for a duration of 3–6 sec through tip 22 and into the scala media. Scientific investigation has indicated that during the 3–6 second refresh periods for electrode 20, the potential across the basilar membrane will persist. Referring to FIG. 9, an additional preferred embodiment of a charge injection assembly 90 permits a continuous injection of charge into the scala media, analogous to full-wave rectification. Patients that have a damaged scala media, which is less capable of storing charge, may prefer this embodiment. Assembly 90 includes a pair of charge injection units 106 and 108, which are toggled in their active states by an electrode driver and switch control assembly 28 controlling ion selective membranes 36 and 38 to maintain a continuous charge injection. Units 106 and 108 include a pair of driving electrodes 120 and 122 respectively, and a pair of tips 124 and 126 respectively. One or more refresh electrodes 130 are used to maintain electrodes 120 and 122, so that an injection of charge into the scala media can be continuously maintained, by switching between tips 124 and 126. In an alternative embodiment, the duty factor of the charge injection is increased, but is still not continuous.

Figure 10:
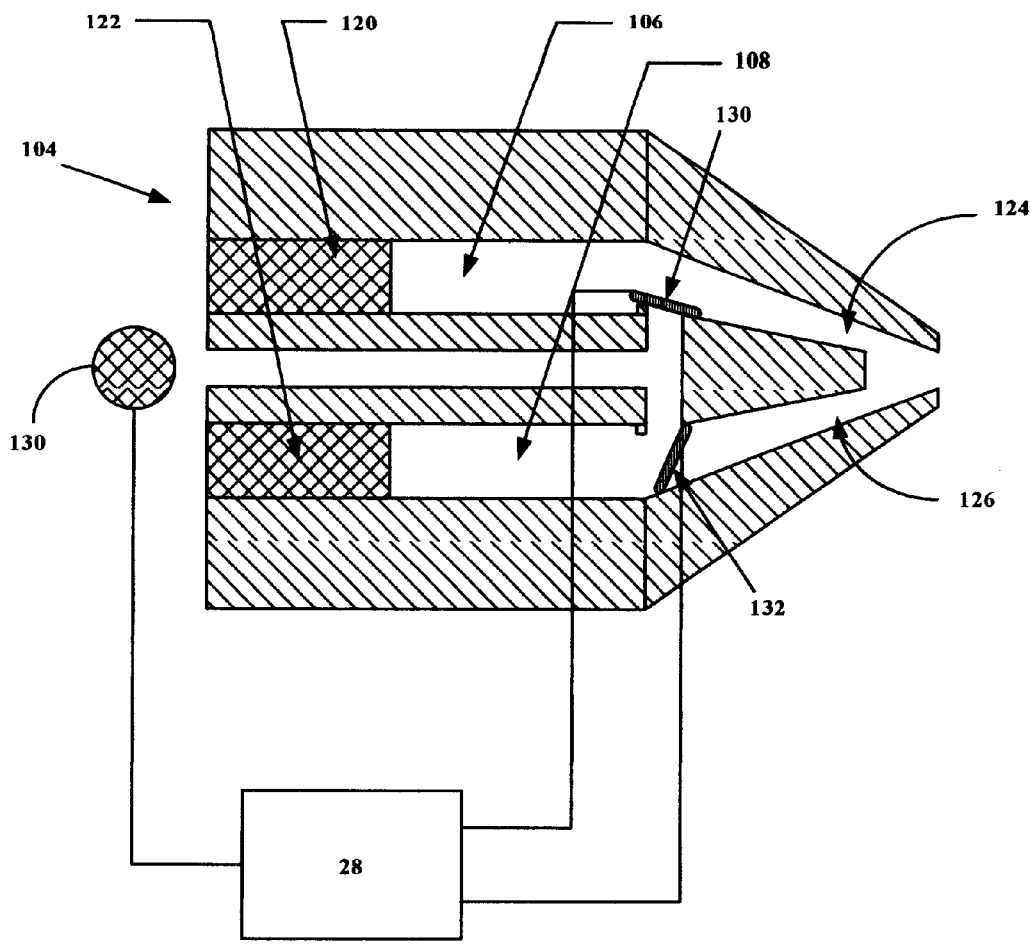
FIG. 10 is an illustration of an additional alternative embodiment of an implantable charge injection assembly, which has two charge injection units, but having a different construction from that of FIG. 9.

Referring to FIG. 10, an alternative embodiment of an assembly 104 is conceptually the same as assembly 90 except for that instead of ion selective membranes 36 and 38 a pair of MEMS switches 130 and 132 are used for alternately occluding unit 106 and 108.

For any of the above described embodiments, the current driver and switch control assembly 28 are sized to drive a maximum current of 5–30 $\mu A$ in either direction. In one preferred embodiment, in which the resistance of unit 12 is 1 MΩ, the driver is designed to remain linear over a range of at least ±30 volts. In another preferred embodiment, the dimensions of unit 12 are altered so as to reduce the resistance of unit 12. In another preferred embodiment the voltage level of the fluid of the scala media is measured and used to regulate the amount of current injected. It is noted that a large peak voltage has the potential for causing damage to body tissue and should generally be avoided.

Figure 11:
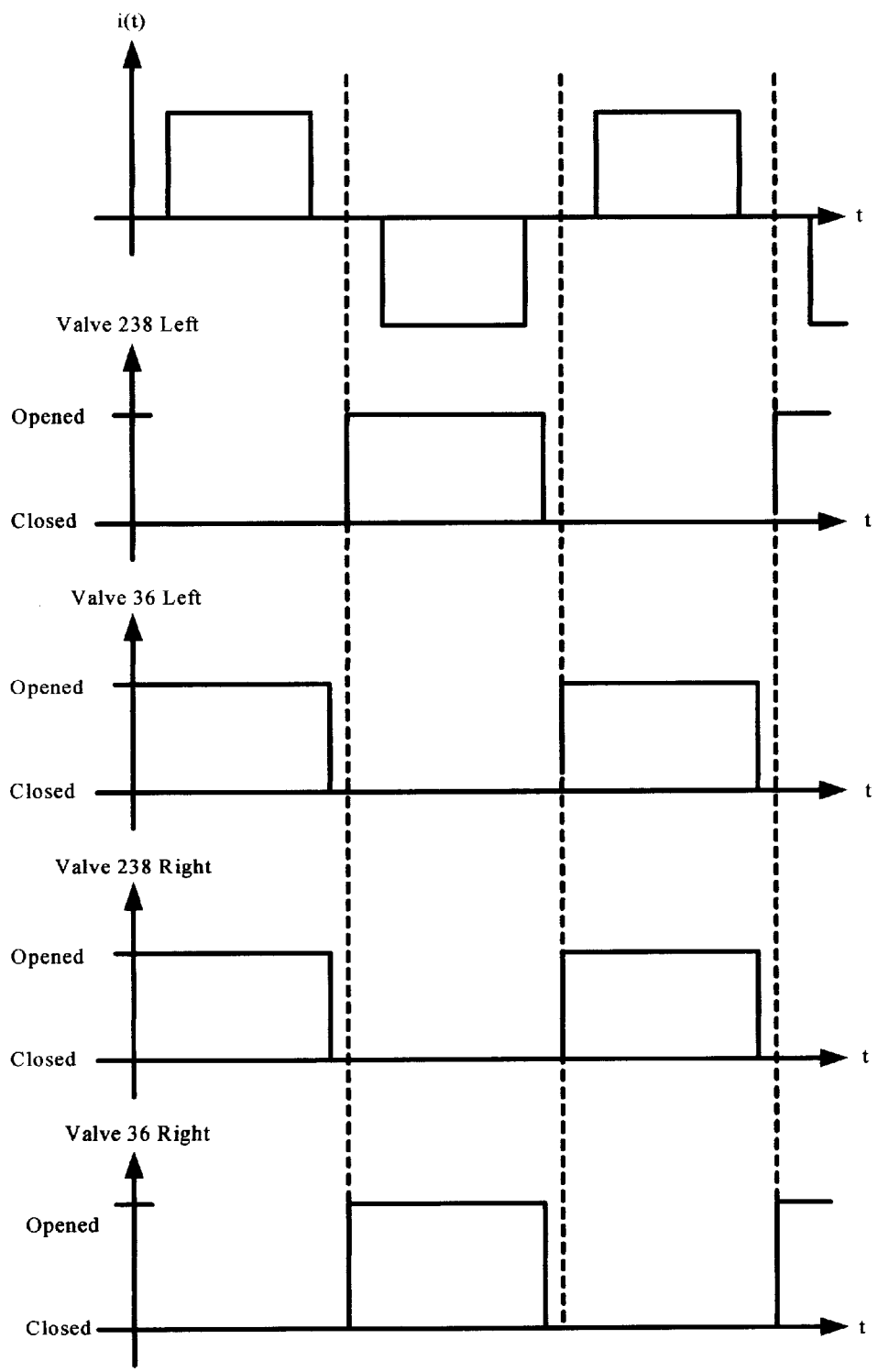
FIG. 11 is a timing diagram for the assembly of FIG. 9, but that would apply equally as well (with analogous labeling) to the embodiment of FIG. 10, and the embodiment of FIGS. 12 and 13.

FIG. 11 shows the logic of assemblies 90, 104 and 210 (referring specifically to FIG. 12 and 13), where i(t) is the current applied from the current generator, and the other graphs in the sketch of the logic show the positions of the MEMS switches. Note that the current drive is discontinuous and that the time that the drive is applied during each half cycle is less than the total time of a half cycle. Current is delayed at the beginning of each half cycle to ensure that the MEMS gates are properly opened and closed before current flows through the system. Current is shut off prior to the end of each half cycle to ensure that no current will be driven during the time that the MEMS gates close. In summary, while current is unidirectional (injected) into the scala media, it is not true DC, but is interrupted.

One problem encountered with the use of the systems described above is that they may permit sodium ions from the body tissue outside the scala media to corrupt the scala media fluid, which is rich in potassium ions. Likewise, potassium ions from the scala media may migrate into and damage body tissue.

Figure 12:
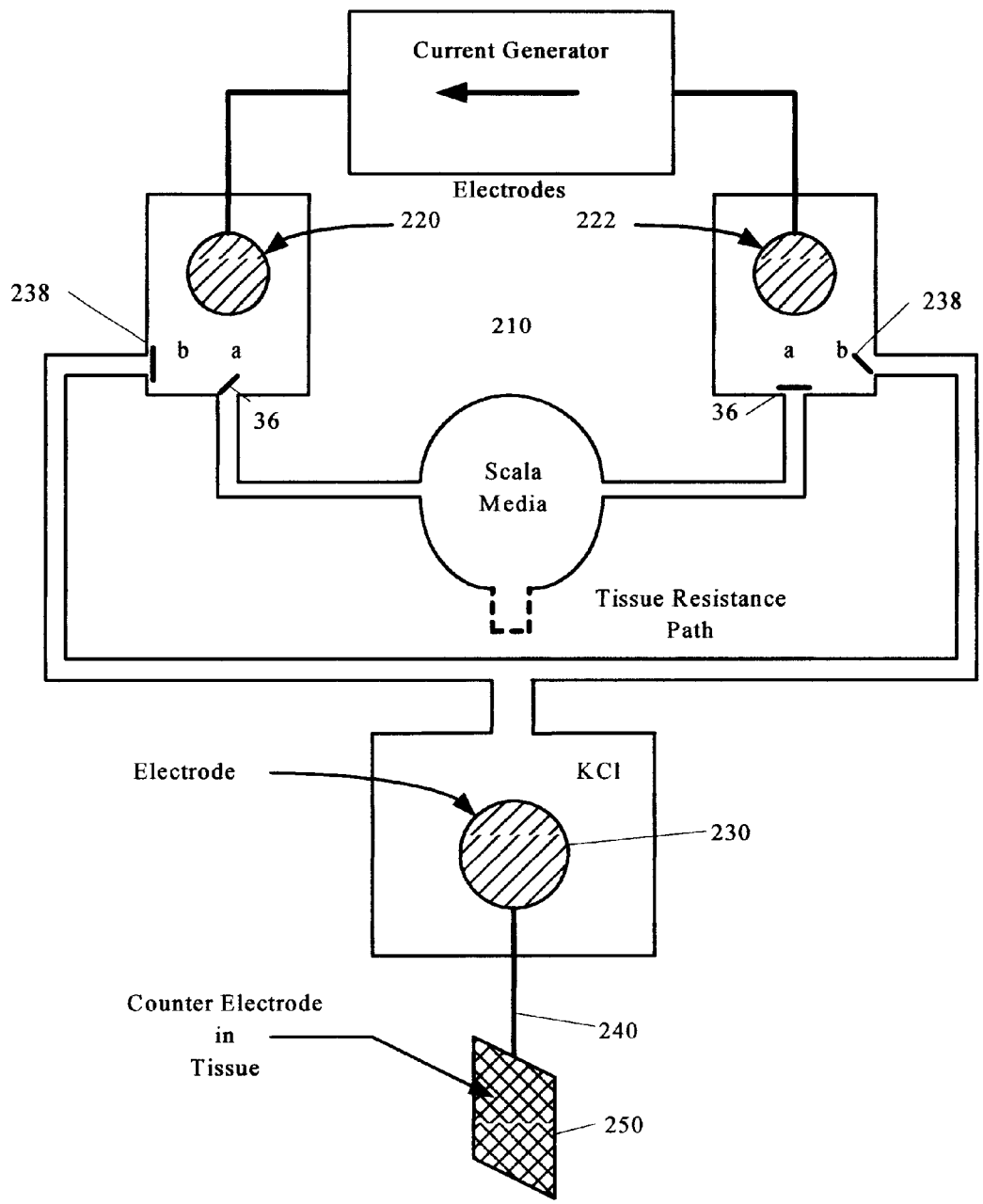
FIG. 12 is a schematic diagram of an additional alternative embodiment of an implantable charge injection assembly, showing the assembly in a first state.
Figure 13:
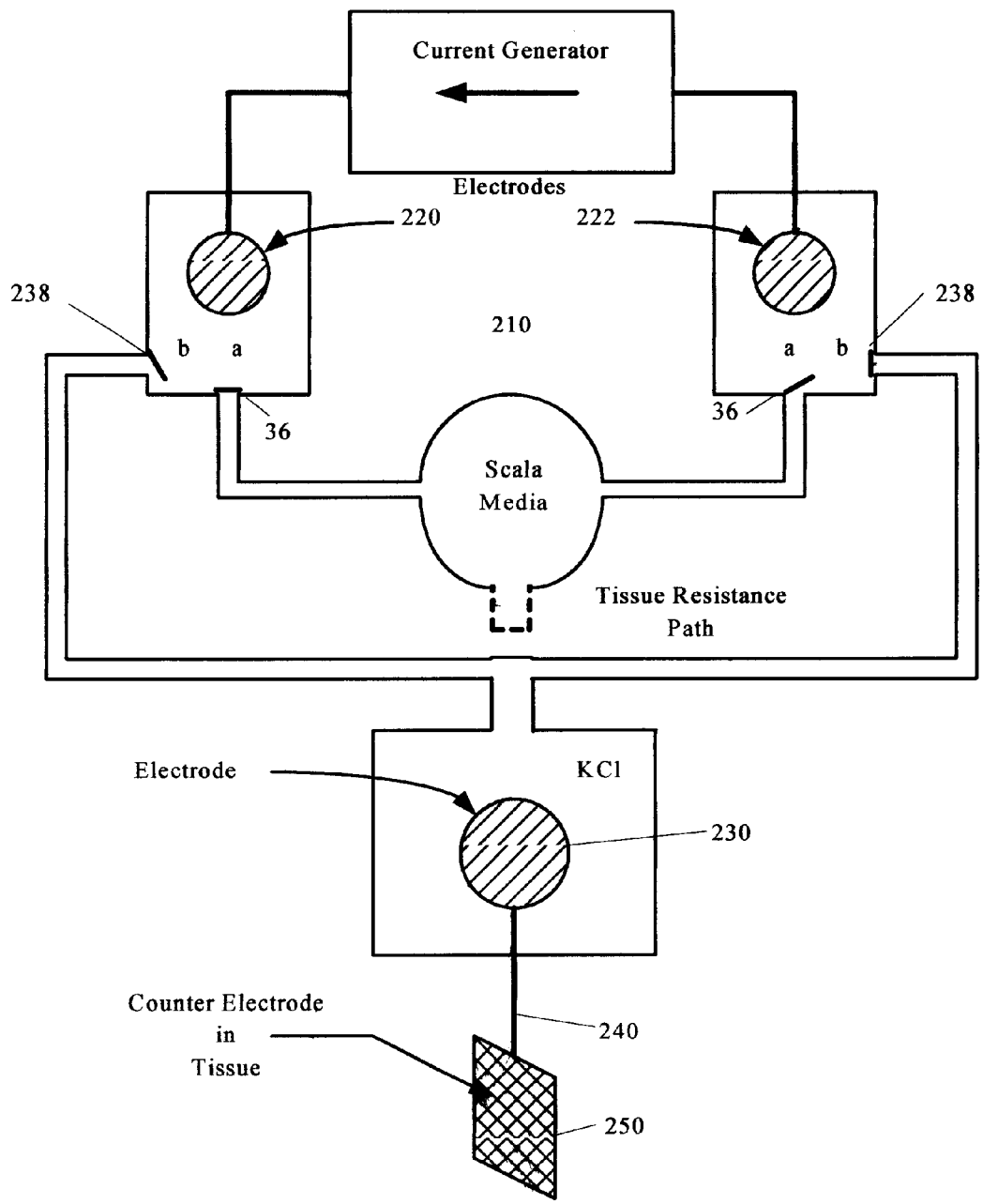
FIG. 13 is a schematic diagram of an additional alternative embodiment of an implantable charge injection assembly, showing the assembly in a second state.

FIGS. 12 and 13 show a charge injection assembly 210 designed to overcome the problem that is outlined in the paragraph above. The assembly 210 is modified to be fully closed and isolated from the tissue, save through a pair of valves 236 leading into the scala media. KCl is confined to the assembly 210 and to the scala media, where it is found naturally. A third metallic electrode 230 is contained in the KCl-filled electrode assembly. That third electrode is connected by a metallic conductor 240 to a fourth electrode 250, which is embedded in the sodium-rich tissues that are external to the scala media via a fourth. This design contains the potassium-rich solutions in tissues where potassium is the normally the dominant ion. It provides a return path for the two active electrodes 220 and 222, by way of valves 238.

FIG. 12 shows the implementation of assembly 210 with current flowing from electrode 220, via the scala media and external tissue, through the external electrode 230 and thence to the right-hand assembly electrode 222, which is negatively charged. FIG. 13 reverses the process.

Since current is not driven with a 100% duty cycle, as is described in the text associated with FIG. 11, the absence of current for a portion of the time, permits the internal electrode 230 and external electrode 250 to depolarize relative to each other.

The terms and expressions which have been employed in the foregoing specification are used as terms of description and not of limitation, and there is no intention, in the use of such terms and expressions, of excluding equivalents of the features shown and described or portions thereof, it being recognized that the scope of the invention is defined and limited only by the claims which follow.

What is claimed is:

1. A method to increase the endocochlear potential within the ear to restore normal hearing comprising implanting an electrical device in the ear and injecting pulses of a unidirectional current flow of at least an average of 5 $\mu$A DC current into the scala media for at least thirty days.

* * * * *

UNITED STATES PATENT AND TRADEMARK OFFICE
CERTIFICATE OF CORRECTION

PATENT NO.    : 6,694,190 B1
DATED         : February 17, 2004
INVENTOR(S)   : Spelman et al.

It is certified that error appears in the above-identified patent and that said Letters Patent is hereby corrected as shown below:

Title page,
Item [73], Assignee, "Lochlear" should be -- Cochlear --; and "Snowqualmie" should be -- Snoqualmie --

Signed and Sealed this

Twenty-fifth Day of May, 2004

JON W. DUDAS
*Acting Director of the United States Patent and Trademark Office*